United States Patent [19]

McDonnell

[11] Patent Number: 5,728,405
[45] Date of Patent: Mar. 17, 1998

[54] METHOD FOR PREVENTING KERATOCYTE LOSS

[75] Inventor: Peter John McDonnell, La Canada-Flintridge, Calif.

[73] Assignee: University of Southern California, Los Angeles, Calif.

[21] Appl. No.: 658,777

[22] Filed: Jun. 5, 1996

Related U.S. Application Data

[63] Continuation of Ser. No. 191,830, Feb. 4, 1994, abandoned.

[51] Int. Cl.$^6$ .............................. A61K 31/74; A61K 9/00
[52] U.S. Cl. .................. 424/682; 424/78.04; 424/428; 514/54; 514/57; 514/59; 514/62; 604/294; 604/295; 604/301; 604/890.1
[58] Field of Search ................... 424/78.04, 428, 424/682; 604/890.1, 294, 295, 301; 514/54, 57, 59, 62

[56] References Cited

U.S. PATENT DOCUMENTS

| | | | |
|---|---|---|---|
| 3,843,782 | 10/1974 | Krezanoski et al. | 424/78 |
| 4,443,432 | 4/1984 | Garabedian et al. | 424/127 |
| 4,581,226 | 4/1986 | Dillon | 424/49 |
| 4,695,536 | 9/1987 | Lindstrom et al. | 435/1 |
| 4,837,021 | 6/1989 | Andermann et al. | 424/602 |
| 4,886,786 | 12/1989 | Lindstrom et al. | 514/54 |
| 4,946,450 | 8/1990 | Erwin | 604/294 |
| 5,104,787 | 4/1992 | Lindstrom et al. | 435/1 |
| 5,143,731 | 9/1992 | Viegas et al. | 424/486 |
| 5,242,902 | 9/1993 | Murphy et al. | 514/12 |
| 5,277,911 | 1/1994 | Viegas et al. | 424/427 |
| 5,318,780 | 6/1994 | Viegas et al. | 424/427 |
| 5,380,537 | 1/1995 | Andermann | 424/602 |

FOREIGN PATENT DOCUMENTS 0 323 522A  7/1988  European Pat. Off.

OTHER PUBLICATIONS

Dohlman, C.H., "The function of the corneal epithelium in health and disease. The Jonas S. Friedenwald Memorial Lecture," *Invest. Ophthalmol.*, vol. 10, No. 6, 383–407 (1971).

Dohlman, C.H. et al., "The effect of the absence of corneal epithelium or endothelium on the stromal keratocytes," *Invest. Ophthalmol.*, vol. 7, No. 5, 520–534 (1968).

Fantes, F. et al., "Wound healing after excimer laser keratomileusis (photorefractive keratectomy) in monkeys," *Arch. Ophthalmol.*, vol. 108, 665–675 (1990).

Hirst, L.W. et al., "Comparative studies of corneal surface injury in the monkey and rabbit," *Arch. Ophthalmol.*, vol. 99, 1066–1073 (1981).

Kaufman, H.E. et al., "Optisol Corneal Storage Medium," *Arch. Ophthalmol.*, vol. 109, 864–868 (1991).

Kenyon, K.R. et al., "Prevention of stromal ulceration in the alkali–burned rabbit cornea by glued–on contact lenses. Evidence for the role of polymorphonuclear leukocytes in collagen degradation," *Invest. Ophthalmol. Vis. Sci.*, vol. 18, No. 6, 570–587 (1979).

Lindstrom, R.L. et al., "Optisol Corneal Storage Medium," *Am. J. Ophthalmol.*, 114, 345–356 (1992).

McDonald, M.B. et al., "One–year refractive results of central photorefractive keratectomy for myopia in the non-human primate cornea," *Arch. Ophthalmol.*, vol. 108, 40–47 (1990).

Nakayasu, K., "Stromal changes following removal of epithelium in rat cornea," *Jpn. J. Ophthalmol.*, vol. 32:113–125 (1988).

Saika, S., "Ultrastructural effect of L–ascorbic acid 2–phosphate on cultured keratocytes," *Cornea* 11(5):439–445 (1992).

Hermann, Heinz et al., "ATP Level, Cell Injury, and Apparent Epithelium–Stroma Interaction in the Cornea", *J. Cell Biol.*, 25:465–71 (1962).

Johnson–Muller et al., "Regulation of Corneal Collagenase Production: Epithelial–stromal Cell Interactions", *Proc. Natl. Acad. Sci.*, 75:4417–4421 (1978).

Chemical Abstracts 106:169003, "The Effect Of a New Intraocular Irrigating Solution Containing Dextran on Rabbit Corneal Epithelium", Polack et al., Apr. 1986.

Medline Abstracts 89036717, "Clinical Uses of Collagen Shields", Poland et al., Sep. 1988.

*Primary Examiner*—Frederick Krass
*Attorney, Agent, or Firm*—Fulbright & Jaworski

[57] ABSTRACT

Keratocyte loss after trauma or injury to the corneal epithelium is prevented or reduced by applying to the corneal epithelium a keratocyte maintenance solution over a period of time sufficient to permit corneal wound healing. The keratocyte maintenance solution is applied to the cornea after trauma (for example, removal of the epithelium prior to surgery, such as photorefractive keratectomy). Preferably, the solution is maintained over the cornea by means of a fluid bath or by means of an absorbent material effective for controlled release of the solution to the cornea (e.g., a collagen shield substantially in the form of a conventional contact lens). A preferred keratocyte maintenance solution is a corneal storage medium.

14 Claims, 1 Drawing Sheet

METHOD FOR PREVENTING KERATOCYTE LOSS

This is a continuation of U.S. Ser. No. 08/191,830, filed Feb. 4, 1994 and now abandoned.

BACKGROUND OF THE INVENTION

The present invention relates generally to the field of medicine. In particular, the present invention is directed to methods of preventing keratocyte loss after trauma to the cornea, in particular during and after corneal surgery.

Corneal wound healing after superficial injury, including excimer laser keratectomy, has been studied extensively. Preliminary studies have shown that an early decrease in the density of keratocytes is followed by an increased number of these cells in the underlying stroma and by production of collagen and extracellular matrix [Fantes, F. et al., "Wound healing after excimer laser keratomileusis (photorefractive keratectomy) in monkeys," Arch Ophthalmol. 108:665–675 (1990); Hirst, L. W. et al., "Comparative studies of corneal surface injury in the monkey and rabbit," Arch Ophthalmol. 99:1066–1073 (1981); Kenyon, K. R. et al., "Prevention of stromal ulceration in the alkali-burned rabbit cornea by glued-on contact lenses. Evidence for the role of polymorphonuclear leukocytes in collagen degradation," Invest Ophthalmol Vis Sci. 18:570–587 (1979)]. This stromal regrowth is related to subepithelial haze in the visual axis and results in a lack of predictability of the refractive result after excimer laser keratectomy. Stromal regrowth also induces instability of the refractive result, making retreatment with the laser more difficult.

Removal of the corneal epithelium is necessary before photorefractive keratectomy. Several techniques, such as mechanical removal alone, the use of chemicals (such as cocaine) to facilitate epithelial removal, or laser ablation have been used for deepithelialization. Results on how the absence of corneal epithelium affects the stromal keratocytes are contradictory. Initial studies demonstrated that metabolites, such as carbohydrates, are exchanged between the epithelium and stroma [Herrmann, H. & Hickman, F. H., "Exploratory studies on corneal metabolism," Bull Johns Hopkins Hosp. 82:225–259 (1948); Herrmann, H. & Hickman, F. H., "Further experiments on corneal metabolism in respect to glucose and lactic acid," Bull Johns Hopkins Hosp. 82:260–272 (1948)]. Other studies suggested that the epithelium influences the cellular activation and metabolic activities of stromal cells during wound healing [Dohlman, C. H., "The function of the corneal epithelium in health and disease. The Jonas S. Friedenwald Memorial Lecture," Invest Ophthamol. 10:383–407 (1971); Johnson-Muller, B. & Gross, J., "Regulation of corneal collagenase production: epithelial-stromal cell interactions," Proc Natl Acad Sci. 75:4417–4421 (1978)]. Although some reports concluded that the loss of stromal cells was related to mechanical trauma, other studies suggested that an atraumatic removal of the epithelium does not prevent changes in the stromal cells [Herrmann, H. & Lebeau, P. L., "ATP level, cell injury, and apparent epithelium-stromal interaction in the cornea," J Cell Biol. 25:465–471 (1962); Nakayasu, K., "Stromal changes following removal of epithelium in rat cornea," Jpn J Ophthalmol. 32:113–125 (1988)]. Recent studies using the excimer laser to perform ablations of the cornea attributed the early keratocyte loss to the excimer laser ultraviolet irradiation itself [McDonald, M. B. et al., "One-year refractive results of central photorefractive keratectomy for myopia in the nonhuman primate cornea," Arch Ophthalmol. 108:40–47 (1990)]. The methods of the studies vary; some examine only immediate changes and others only very delayed changes, and still others utilized histologic studies at the light microscopic level only. The experimental animals have included rats, rabbits and guinea pigs, but rarely primates. Information on the interactions between the corneal epithelium and underlying stroma may improve understanding of wound healing after refractive procedures such as photorefractive keratectomy.

U.S. Pat. No. 5,104,787 (the entire disclosure of which is hereby incorporated by reference) describes compositions and methods for preservation of eye tissue, particularly corneal tissue, between removal from the donor and transplantation. No other specific use for the corneal storage solutions is disclosed; in particular, there is no suggestion of the use of the solutions in in vivo treatments.

It is an object of the present invention to provide compositions and methods for use in preventing keratocyte loss after trauma to the cornea, in particular during and after corneal surgery.

SUMMARY OF THE INVENTION

In accordance with the present invention, keratocyte loss after trauma to the corneal epithelium is prevented or reduced by applying to the corneal epithelium a keratocyte maintenance solution (as hereinafter defined) over a period of time sufficient to permit corneal epithelial wound healing. Pursuant to the invention, the keratocyte maintenance solution is applied to the cornea after trauma (for example, removal of the epithelium prior to surgery, such as photorefractive keratectomy). Pursuant to one preferred embodiment, the solution is maintained over the cornea by means of a fluid bath. In a particularly preferred embodiment of the invention, the solution is maintained in contact with the cornea by means of an absorbent material effective for controlled release of the solution to the cornea.

BRIEF DESCRIPTION OF THE DRAWINGS

The invention may be better understood with reference to the accompanying drawings, in which.

DETAILED DESCRIPTION OF THE INVENTION

Figure 1:
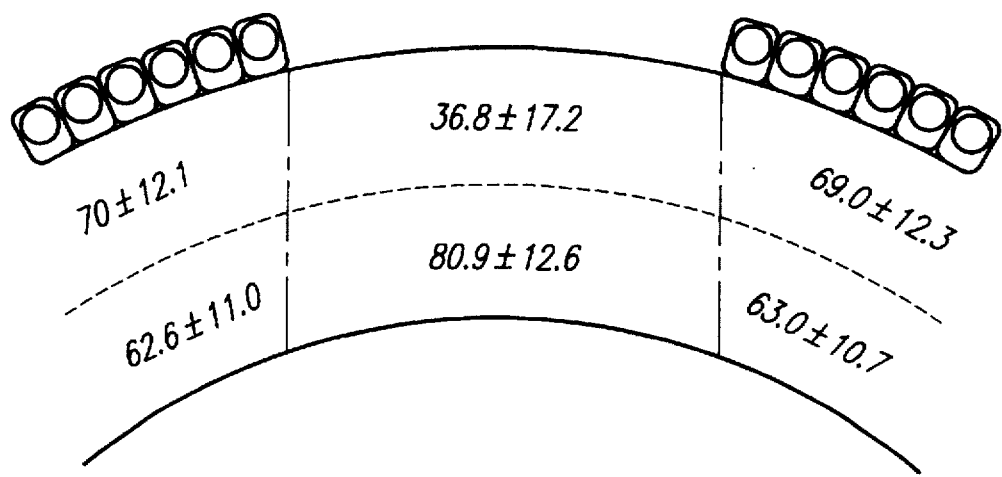
FIG. 1 represents a schematic section of the rabbit cornea showing the number of keratocytes present in each of the studied areas.
Figure 2:
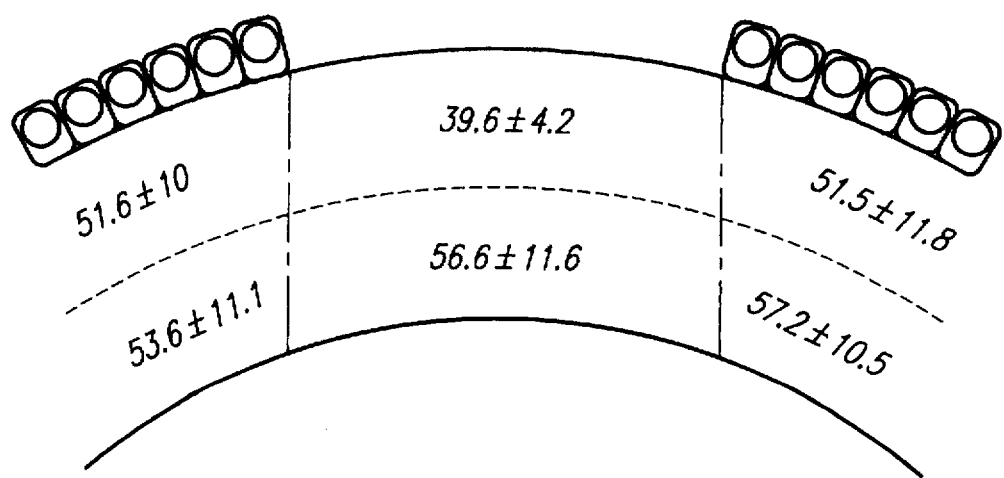
FIG. 2 represents a schematic section of the monkey cornea showing the number of keratocytes present in each of the studied areas.

Pursuant to the present invention, damage to the cornea following trauma thereto resulting in at least some injury to the epithelium is prevented or minimized by applying to the corneal epithelium a keratocyte maintenance solution over a period of time sufficient to permit corneal wound healing. The method of the present invention is particularly useful in promoting healing after surgery which involves removal or disruption of the corneal epithelium, including but not limited to the following procedures: photorefractive keratectomy, keratomileusis, epikeratophakia, lamellar keratectomy, radial keratotomy, corneal transplantation, and other intraocular surgical procedures. In addition, healing of the cornea is promoted in accordance with the present invention following scraping of the corneal epithelium for other reasons such as epithelial debridement to improve visibility during intraocular surgery) or any type of trauma resulting in some injury to the epithelium, such as laceration or abrasion of the eye (caused, for example, by a superficial corneal foreign body).

For purposes of the present invention, a keratocyte maintenance solution is defined as a solution which enhances keratocyte viability by maintaining normal physiologic metabolism. A fairly wide variety of solutions may be employed for this purpose. To determine rapidly whether a particular solution as hereinafter described would be suitable for use in accordance with the present invention, the behavior of cells from a culture of keratocyte cells [see Saika, S., "Ultrastructural effect of L-ascorbic acid 2-phosphate on cultured keratocytes," *Cornea* 11:439–445 (1992)] brought into contact with the solution may be observed. Solutions clearly not suitable for use as keratocyte maintenance solutions cause the cells to become enlarged, and ultimately to rupture. On the other hand, keratocytes exhibit a normal, healthy appearance even after several hours in contact with a suitable keratocyte maintenance solution.

A primary consideration for formulation of a suitable keratocyte maintenance solution is the osmolarity thereof. In contact with low osmolarity (hypotonic) solutions, the keratocytes do not survive for very long periods of time. Accordingly, a keratocyte maintenance solution in accordance with the present invention will have an osmolarity of at least about 250 mOsm. Preferably, the osmolarity of the solution is at least about 280 mOsm, and most preferably, at least about 320 mOsm. One particularly useful manner in which to provide solutions with high osmolarity is the inclusion therein of one or more non-immunogenic macromolecules. Examples of such materials include, but are not limited to, the following: glycosaminoglycans (e.g., chondroitin sulfate, dermatan sulfate, dermatin sulfate, heparin sulfate, heparan sulfate, keratin sulfate, keratan sulfate and/or hyaluronic acid); low or high molecular weight polysaccharides, such as dextran; dextran sulfate; polyvinyl pyrrolidone; polyethylene glycol; polyvinyl acetate; hydroxypropyl cellulose; hydroxypropylmethyl cellulose; carboxymethyl cellulose; and carboxypropylmethyl cellulose. Neutral or negatively-charged macromolecules are particularly suitable for use in this regard. While the concentration of macromolecule may be varied over a fairly broad range as appropriate to provide a solution with the desired osmolarity, it is presently preferred that the at least one macromolecule comprise about 0.1% to about 10% by weight of the keratocyte maintenance solution.

In addition, it has been determined that a suitable keratocyte maintenance solution must contain at least one of magnesium and calcium, and preferably both. While the present invention is not bound to any particular theory, it is believed that the presence of at least one of magnesium and calcium is necessary to maintain enzyme activity and proper keratocyte cell binding in the cornea during reepithelialization. In addition, it is preferred that the keratocyte maintenance solution comprise other ions (for example, $Na^+$, $K^+$, $Cl^-$, etc.) which are generally recognized in the art as useful in maintaining normal cell growth in, e.g., cell culture solutions.

It is further considered to be desirable to include a suitable buffer system in the keratocyte maintenance solution so as to provide a composition which has a pH roughly comparable to physiological pH. In general, any of the art-recognized buffer systems which are suitable to provide a pH in the range of about 6.8 to about 7.6 would be useful for this purpose. Suitable buffer systems include, but are not limited to, bicarbonate buffer systems, HEPES buffer systems and mixtures thereof.

One class of materials suitable for use in accordance with the present invention are a number of compositions which have heretofore been employed as corneal storage media. As is well known in the art, corneal storage media comprise mixtures of components selected from balanced salts, amino acids, energy sources, antioxidants, buffering agents, cell membrane stabilizers, glycosaminoglycans, deturgescents and antibiotics. Antibiotics and antimycotics in the media are useful for preventing infection (i.e., to suppress growth of bacteria or fungi), rather than for keratocyte maintenance and growth; accordingly, they are considered an optional component of the preferred compositions for use in accordance with the present invention. Similarly, for purposes of the present invention various additional components conventionally included in the heretofore-known corneal storage media (for example, antioxidants, cell membrane stabilizers, ATP precursors, and nutrient cell supplements), may be included in accordance with particular embodiments of the present invention but are not presently considered essential for maintenance of keratocytes. One particularly useful composition for purposes of the present invention is a corneal storage medium containing chondroitin sulfate, available commercially from Chiron Ophthalmics, Inc., Irvine, Calif. under the trade designation Optisol™ [Kaufman, H. E. et al., "Optisol Corneal Storage Medium," *Arch Ophthalmol* 109, 864–868 (1991); Lindstrom, R. L. et al., "Optisol Corneal Storage Medium," *Am. J. Ophthalmol.* 114, 345–356 (1992)].

Presently preferred for use in accordance with the present invention are the corneal storage media as generally disclosed in the aforementioned U.S. Pat. No. 5,104,787. As more fully described therein, in general these solutions contain an aqueous nutrient and electrolyte solution, at least one glycosaminoglycan, at least one deturgescent agent, at least one energy source, at least one buffer system, at least one antioxidant, at least one antibiotic, at least one membrane stabilizing component, at least one ATP precursor and nutrient cell supplements, all in amounts sufficient to enhance cell viability and metabolism and wound healing.

Nutrient and electrolyte solutions, which are well defined in the art of tissue culturing, contain the essential nutrients and electrolytes at at least the minimal concentrations necessary for cell maintenance and growth. In general, they contain inorganic salts (e.g., calcium, magnesium, iron, sodium and potassium salts of carbonates, nitrates, phosphates, chloride and the like), essential and non-essential amino acids, vitamins and other essential nutrients. Suitable basal nutrient media are commercially available, for example from Gibco Laboratories, Grand Island, N.Y. and Microbiological Associates, Walkersville, Md. under the designations TC199 and Eagle's Minimal Essential Medium (MEM). As more fully explained in U.S. Pat. No. 5,104,787, these and similar nutrient media (or mixtures of one or more thereof) serve as the basis for formulating corneal storage media as are particularly suitable for use in accordance with the present invention. Of course, for purposes of the present invention the presence of at least one of magnesium and calcium is considered essential; inclusion of other typical components of conventional basal nutrient media useful in the maintenance of cell growth (e.g., other salts, amino acids and vitamins, etc.) is preferred.

Particularly preferred compositions (as described in U.S. Pat. No. 5,104,787) for use in accordance with the present invention comprise the following: an aqueous electrolyte solution (e.g., Minimal Essential Medium and/or TC199); a glycosaminoglycan (e.g., standard or purified high or low molecular weight A, B or C isomers of chondroitin sulfate, dermatan sulfate, dermarin sulfate, heparin sulfate, heparan sulfate, keratin sulfate, keratan sulfate and/or hyaluronic acid) in a range of 0.01 mg/ml to 100 mg/ml; a deturgescent agent (e.g., low or high molecular weight polysaccharide, such as dextran, dextran sulfate, polyvinyl pyrrolidone, polyethylene glycol, polyvinyl acetate, hydroxypropylmethyl cellulose, carboxymethyl cellulose, carboxypropylmethyl cellulose, etc.) in a range of 0.01 mg/ml to 100 mg/ml; an energy and carbon source (e.g., glucose, pyruvate, sucrose, fructose and/or dextrose) in a range of 0.05 mM to 10 mM; a buffer system (e.g., a bicarbonate buffer system, HEPES buffer, etc.) to maintain a physiologic pH (desirably between about 6.8 and about 7.6) in a range of 0.1 mM to 100 mM; optionally, an antioxidant (e.g., ascorbic acid, 2-mercaptoethanol, gluthathione and/or alpha tocopherol) in a range of 0.001 mM to 10 mM; optionally, membrane stabilizing agents (e.g., vitamins A and B, retinoic acid and/or other cofactors, ethanolamine, phosphoethanolamine, selenium and/or transferrin) in a range of 0.01 mg/ml to 500 mg/ml; optionally, for purposes of the present invention, antibiotics and/or antimycotic agents (e.g., amphotericin B, gentamicin sulfate, kanamycin sulfate, neomycin sulfate, nystatin, penicillin, tobramycin, streptomycin sulfate) in a range of 0.1 µg/ml to 1 mg/ml; optionally, ATP precursors (e.g., adenosine, inosine, adenine) in a range of 0.001 mM to 10 mM; and optionally, nutrient cell supplements (e.g., cholesterol, L-hydroxyproline, d-biotin, calciferol, niacin, para-aminobenzoic acid, pyridoxine HCl, vitamin B12, $Fe(NO_3)_3$ and/or non-essential amino acids) in a range of 0.001 mM to 10 mM. As noted in U.S. Pat. No. 5,104,787, the solutions are preferably serum free.

One particularly preferred solution according to U.S. Pat. No. 5,104,787 has the following composition: as aqueous nutrient and electrolyte solution, Eagle's Minimal Essential Medium (MEM); as a glycosaminoglycan, 2.5% chondroitin sulfate; as a deturgescent agent, 1% dextran; as an energy source, 110 mg/L pyruvate and 1000 mg/L glucose; as a buffer system, 2200 mg/L bicarbonate buffer and 25 mM HEPES buffer; optionally, as antioxidant, 0.05 mM 2-mercaptoethanol and 0.01 mg/L alphatocopherol; optionally, as antibiotic and/or antimycotic, 100 mg/L gentamicin sulfate; as ATP precursors, 5 mg/L adenosine, 10 mg/L inosine and 10 mg/L adenine; and optionally, as nutrient cell supplements, 0.2 mg/L cholesterol, 10 mg/L L-hydroxyproline, 0.01 mg/L d-biotin, 0.1 mg/L calciferol, 0.025 mg/L niacin, 0.05 mg/L para-aminobenzoic acid, 0.25 mg/L pyridoxine HCl, 1.36 mg/L vitamin B12, 0.5 mg/L $Fe(NO_3)_3$ and 0.1 mM non-essential amino acids. The solution is free of serum, glutathione and any structural analogue of reduced glutathione.

In accordance with the invention, the keratocyte maintenance solution may be either periodically applied to or maintained continuously or substantially continuously in contact with the cornea for a period of time sufficient to permit corneal wound healing. While the amount of time required for healing (which, for purposes of the present invention, refers in particular to closure of the epithelial defect) will of course vary with the particular patient, it is generally appropriate to maintain the solution in regular periodic or continuous contact with the cornea for a period of time on the order of at least about 12 hours to about one week, and preferably about 24 to about 72 hours.

In accordance with one embodiment of the present invention, a quantity of the keratocyte maintenance solution sufficient to substantially coat the surface of the corneal epithelium (e.g., about 20 µl to about 100 µl, preferably about 50 µl) is periodically applied to the corneal surface at a rate sufficient to maintain (or substantially maintain) normal keratocyte metabolism. Such application may be effected manually (for example, by means of an eyedropper) or automatically (for example, by automated dropper means). It has been determined that application of one or two drops of keratocyte maintenance solution at a rate of once about every 5 minutes to once about every hour, preferably once about every ten minutes to once about every half-hour, and most preferably once about every fifteen minutes, is sufficient to maintain (or substantially maintain) normal keratocyte metabolism.

Pursuant to one preferred embodiment, the solution is maintained over the cornea as a fluid bath. This can be achieved, for example, by maintaining a quantity of the solution over the cornea in a glass or plastic container. The solution in the container may be periodically replenished or replaced, preferably on a daily basis.

In a particularly preferred embodiment of the invention, the solution is maintained in contact with the cornea by means of a piece of an absorbent material (for example, in the form of a lens or a shield having roughly the dimensions of a conventional contact lens) effective for controlled release of the solution to the cornea. While a variety of materials are suitable for this purpose, one particularly preferred material comprises a collagen shield in the shape of a contact lens. Such collagen shields are available commercially, for example from Chiron Ophthalmics, Inc., Irvine, Calif. under the designations SurgiLens™ and MediLens™. The collagen shield is suitably soaked in the keratocyte maintenance solution for several minutes to absorb the solution. Thereafter, the solution-impregnated shield is applied to the eye and maintained in place during the healing period. A particular advantage of this embodiment of the invention is that the collagen shield dissolves in situ over a period of time which in many cases is sufficient to permit corneal healing. Collagen seems to be advantageous as a biomaterial for these purposes due to its mechanical and biological properties. One important therapeutic benefit appears to be a reduction in mechanical trauma to the epithelium, due to lubrication and protection of the corneal surface, secondary either to lid abnormalities or to normal blinking. This may reduce pain and potentiate the process of epithelial adhesion to the underlying tissue.

In the course of developing the present invention, it was confirmed that stromal keratocytes are affected by the absence of overlying corneal epithelium. Keratocyte loss alters the normal course of corneal wound healing, and thus the corneal clarity or refractive outcome. The ultrastructural effects of the absence of epithelium on stromal keratocytes in rabbits and primates were further investigated and quantitated, and the effect of the absence of epithelium on the healing of stromal incisions in rabbit cornea was examined. As a consequence of these studies, a method to prevent the keratocyte loss caused by deepithelialization was developed.

Rabbits and monkeys were used in these studies. The results obtained in both species were comparable, although the acellular zone in the denuded stroma 24 hours after surgery appears to be greater in the rabbit. The importance of this finding is that the presence of Bowman's membrane in the monkeys did not prevent rapid degeneration of the keratocytes after deepithelialization.

The onset of the ultrastructural changes in keratocytes in response to superficial corneal injury was early in the postoperative period. These cellular degenerative changes in the rabbit cornea were visible with transmission electron microscopy as early as 15 minutes after scraping. Keratocyte changes in the most anterior aspect of the stroma of rabbit cornea were observed within 30 minutes of epithelial removal; this short time course suggests that osmotic injury may account for the cell damage. The changes observed here cannot be ascribed solely to corneal swelling, as it has been reported that the absence of corneal endothelium caused no apparent loss of stromal keratocytes even in the presence of intense corneal edema [Dohlman, C. H. et al., "The effect of the absence of corneal epithelium or endothelium on the stromal keratocytes," *Invest Ophthalmol.* 7:520–534 (1968) ]. At six hours after surgery, the corneal epithelium showed initial signs of migration over the denuded stroma. Invasion of the corneal stroma by polymorphonuclear leukocytes (PMNs) was also first apparent at this time. The presence of PMNs in the stroma might be related to the regeneration of the epithelium itself or be stimulated by chemotactic factors liberated by the degenerating keratocytes. The timing of all of these findings suggests an interaction not only between the epithelium and keratocytes, but also between epithelium and PMNs. Clinically, this may contribute to melting of the underlying stroma in persistent epithelial defects.

To examine for effects of epithelial removal on wound healing after refractive surgery, keratotomy incisions in normal and deepithelialized rabbit corneas were studied. At 24 hours postoperatively the wounds in the denuded corneas showed an intense inflammatory response and an absence of keratocytes. Incisions in non-deepithelialized corneas showed only minimal inflammation and keratocytes present adjacent to the incision. Studies of similarly treated corneas 14 days postoperatively showed advanced wound healing in both corneas, but the deepithelialized cornea showed a larger epithelial plug and retraction of the stroma. These results suggest that creation of an epithelial defect may alter wound morphology. The induced retraction of the stroma might increase the wound gape, and consequently increase the refractive effect of linear radial incisions.

In all animals studied, including the monkeys, epithelial denudation of the cornea prior to refractive procedures induced death of anterior stromal keratocytes. Since this occurs in monkeys, which have a Bowman's layer, it likely occurs in the human cornea as well.

While the present invention is not bound to any particular theory, it is believed that a metabolic interaction occurs between the epithelium and the underlying stroma and its cells. The epithelium represents a barrier between the tear film fluids and the environment within the corneal stroma. Exposing the keratocytes to the precorneal tear film appears to result in rapid degenerative changes in these cells. The use of topical metabolic nutrients may reduce the deleterious effects of epithelial removal by maintaining a physiologically acceptable stromal environment and facilitating normal metabolic processes. Denudation of the cornea followed by application of a composition in accordance with the present invention limits keratocyte damage and speeds reepithelialization. These compositions are rich in cellular nutrients, such as glucose, in which the tear film may be relatively deficient. Also, the compositions are higher in osmolarity than is the precorneal tear film and many commercially-available tear film substitutes. These findings suggest that the compositions of the present invention may protect keratocytes and modify corneal wound healing, possibly by preventing osmotic damage to the stromal keratocytes.

The invention may be better understood with reference to the accompanying examples, which are intended for purposes of illustration only and should not be construed as in any sense limiting the scope of the invention as defined in the claims appended hereto.

EXAMPLE 1

Use of Keratocyte Maintenance Solution

A total of fourteen New Zealand Albino rabbits and four monkeys (*Macaca fascicularis*) were used in these studies. Animals were anesthetized with an intramuscular injection of ketamine hydrochloride (40 mg/kg) and xylazine hydrochloride (7 mg/kg). The eyelids were held open with a wire speculum for the duration of the procedure. The animals underwent a unilateral 6 mm mechanical deepithelialization using a Paton spatula. The contralateral eyes were used as controls. No topical medication was applied before or after surgery, with exception of two rabbits that were operated on under a fluid bath.

Eight of the rabbits and all four monkeys were used in this experiment to evaluate the time course of the changes that occur in the stromal keratocytes after deepithelialization. The rabbits were sacrificed at 15 minutes (1 rabbit), 30 minutes (1 rabbit), 2 hours (1 rabbit), 6 hours (1 rabbit) and 24 hours after surgery (4 rabbits); all the monkeys were sacrificed 24 hours after the deepithelialization.

To evaluate the effects of the absence of epithelium on the outcome of linear keratotomies, four rabbits underwent unilateral deepithelialization of the central 6 mm of the cornea as described above. Both eyes from each of these rabbits then underwent a single linear incision, 5 mm in length, using a diamond blade set for 50% of the paracentral depth, as measured by an ultrasonic pachymeter. One rabbit was sacrificed 24 hours after the operation and another rabbit was sacrificed 14 days after surgery. Two rabbits each underwent corneal deepithelialization of one eye under a fluid bath. A clear plastic cylinder containing Optisol™ or sterile isotonic sodium chloride (0.9%) was placed on the globe, while the cornea was deepithelialized. By this method, the solutions were kept in contact with the cornea during the deepithelialization and for one hour postoperatively, at which time the animals were sacrificed. Two rabbits underwent corneal deepithelialization under ambient conditions, but for the following 16 hours a composition in accordance with the present invention was applied topically to one of these animals at 30 minutes intervals; the other animal did not receive any topical solution after deepithelialization.

After enucleation, all eyes were immediately prepared in identical fashion for light microscopy and transmission electron microscopy. The whole globes were immersed in half-strength Karnovsky fixative (2% paraformaldehyde, 2.5% glutaraldehyde, and 0.1M sodium cacodylate buffer). The globes were fixed at physiologic pressure by infusion of fixative into the vitreous cavity. After 48 hours of fixation, the corneas were trephined and bisected.

For transmission electron microscopy, one half of each cornea was washed in 0.1M sodium cacodylate buffer, postfixed in 2% osmium tetroxide in 0.1M sodium cacodylate buffer for two hours, washed in 0.1M sodium cacodylate buffer, dehydrated in a graded series of alcohol and then in pure polypropylene oxide, and embedded under vacuum in epoxy plastic resin. For light microscopy, after usual preparation, sections were stained with hematoxylin and eosin. For transmission electron microscopy, 60–80 nm thick sections were cut with a diamond knife ultramicrotome. Tissue was mounted on copper grids and stained with uranyl acetate-lead citrate. The examination of the specimens were performed by an experienced ophthalmic pathologist masked as to the treatment group.

To quantitate the histologic changes observed 24 hours postoperatively, sections were placed under a light microscope (Zeiss, Germany). The sections of the corneas studied were divided into central (corresponding to the deepithelialized zone) and two peripheral (unoperated zone with intact epithelium) areas. The central and peripheral areas were further divided, so as to differentiate anterior from posterior stroma. Keratocyte nuclei were counted within each of the six regions of the cornea and morphologic features were recorded by a single experienced ophthalmic pathologist who was masked as to the treatment groups. Keratocyte counts and morphology between the central anterior stroma (beneath the area of deepithelialization) and the other regions of the stroma were compared.

Measurements of variance and contrast were used to compare the results obtained in the different experimental groups. An overall P<0.05 was considered to be significant.

Within 30 minutes of removal of the central 6 mm of rabbit corneal epithelium, the superficial keratocytes beneath the denuded area showed dilatation of the endoplasmic reticulum and presence of lacunae at the cell margin. This contrasted with the keratocytes located under intact epithelium in the peripheral cornea and in the posterior stroma, which retained a normal appearance. The changes observed in the superficial keratocytes increased with time postoperatively. At six hours after surgery, the stroma was thicker and the keratocytes showed large numbers of intracytoplasmic vacuoles. These changes were greatest within the anterior 100 microns of the stroma, where discontinuities in the keratocyte cell membranes were observed. At this point, polymorphonuclear leukocytes were first seen at the margin of the operated area, and pyknotic changes were first observed by light microscopy in anterior stromal keratocytes. Twenty-four hours after deepithelialization, keratocytes were absent from the anterior 25% of the stroma underneath the deepithelialized area. Electron microscopic examination of the corneas enucleated at this time point showed keratocytes in advanced stages of degeneration within the anterior stroma.

The primate corneas were evaluated 24 hours after deepithelialization. At this time, keratocytes were absent in the anterior stroma and no keratocytes were seen within 75 µm of Bowman's layer. The epithelium showed early signs of migration over the denuded region. In unoperated corneas, normal keratocytes were seen just underneath the Bowman's layer within about 13 microns of the epithelial basement membrane. Ultrastructurally, normal keratocytes were observed about 75 microns deep to Bowman's layer, compared to 13 microns in normal unoperated monkey cornea. Some remnants of keratocytes were seen within the anterior stroma.

An experienced ophthalmic pathologist, masked as to animal species and treatment protocol, reviewed histologic sections of each cornea and counted the keratocyte nuclei within six regions of the stroma. Quantitation of keratocyte loss observed at 24 hours postoperatively in rabbits and monkeys is shown in FIGS. X and X, respectively. The values represent mean±standard deviation. The number of keratocytes identified in the central anterior stroma was compared with the number of keratocytes obtained in the other five areas studied (Table 1). In control eyes of both rabbits and monkeys, the number of keratocytes present in the central stroma beneath the area of epithelial removal (central 6 mm) was similar to the number of keratocytes counted in the other areas. However, in the deepithelialized eyes the number of keratocytes in the anterior central stroma was significantly reduced ($P=0.0001$ in rabbits and $P=0.0007$ in monkeys). In addition, remaining keratocyte nuclei within the superficial central stroma, beneath the zone of deepithelialization, appeared pyknotic compared to those in the five remaining stromal regions.

TABLE 1

Counts of Keratocytes Performed in Deepithelialized and Unoperated Rabbit and Monkey Corneas

| | Anterior Central Stroma | Remaining Stroma | P value |
|---|---|---|---|
| Deepithelialized rabbit corneas | 36.8 ± 17.2 | 69.0 ± 11.7 | .0001 |
| Control | 94.3 ± 12.7 | 76.7 ± 19.7 | .1 |
| Deepithelialized monkey corneas | 39.6 ± 4.2 | 54.1 ± 11.0 | .0007 |
| Controls | 59.4 ± 7.6 | 76.7 ± 6.9 | .49 |

Removal of central epithelium prior to linear keratotomies resulted in altered wound morphology. At 24 hours postoperatively, the keratotomy incisions in the normal corneas showed an early invasion of epithelial cells in the wound. Keratocytes were present immediately adjacent to the incision and appeared normal. A few polymorphonuclear leukocytes were observed in the vicinity of the wound, and slight retraction of the adjacent stroma was seen. Examination of the keratotomy wounds performed in the centrally deepithelialized corneas showed a marked retraction of the adjacent stroma, an intense acute inflammatory response in the stroma and the presence of debris and polymorphonuclear leukocytes within the incisions. In contrast to the control corneas, no keratocytes were observed in the anterior stroma or adjacent to the wound. Fourteen days postoperatively, examination of the keratotomy incisions performed in both unoperated and deepithelialized corneas showed presence of fibrocytes and fibrosis underneath the epithelial plug. The accentuated retraction observed in the early postoperative period in the deepithelialized corneas caused enlargement of the epithelial plugs and the stromal wounds when compared with the non-deepithelialized corneas.

The use of a composition in accordance with the present invention as a nutrient solution during and immediately after deepithelialization of rabbit corneas resulted in healthy superficial keratocytes, as seen by transmission electron microscopy, but early signs of keratocyte damage could be observed in the isotonic saline solution treated corneas. Light microscopic examination of the corneas treated topically at 30 minute intervals with a composition in accordance with the present invention for 16 hours postoperatively revealed preservation of keratocytes and an apparently faster reepithelialization than in the untreated corneas.

EXAMPLE 2

Use of Collagen Shields in Conjunction with Keratocyte Maintenance Solution

Twelve New Zealand white rabbits, 2.0 to 2.5 kg, male and female, were used. All procedures were performed on anesthetized rabbits (ketamine hydrochloride, 40 mg/kg and xylazine, 7 mg/kg). All rabbits were examined preoperatively with a biomicroscope. After being anesthetized, the eyelids were held open with a wire speculum for the duration of the procedure. The animals underwent a bilateral 6 mm mechanical deepithelialization using a blunt Paton spatula (Storz Ophthalmic Instruments, St. Louis, Mo.), with uniform pressure applied during the scraping.

Rabbits were divided into six groups with two rabbits in each group. Surgery was performed uneventfully in all eyes.

Immediately after ablation, the treated areas had a uniform appearance. The groups were treated postoperatively for 24 hours as follows: Group 1, saline drops every four hours; Group 2, drops of a keratocyte maintenance solution in accordance with the present invention including antibiotic (the commercially-available Optisol™ solution) every four hours; Group 3, collagen shields containing chondroitin sulfate (available commercially as MediLens™ from Chiron IntraOptics, Inc., Irvine, Calif.) soaked in sterile saline fitted over the wounded cornea plus saline drops every four hours; Group 4, collagen shields (MediLens™-CS) soaked in Optisol™ plus Optisol™ drops every four hours; Group 5, collagen shields (available commercially as SurgiLens™ from Chiron IntraOptics, Inc.) soaked in sterile saline plus saline drops every four hours; and Group 6, collagen shields (SurgiLens™) soaked in Optisol™ plus Optisol™ drops every four hours. The collagen shields were soaked in the keratocyte maintenance solution or saline solution for 10 minutes before being placed on the rabbit corneas. The drops were applied every four hours. The animals were sacrificed at 24 hours after surgery, the corneas fixed and keratocytes quantitated within anterior and posterior cornea in the area underneath the epithelial defect.

After sacrificing the animals, the corneas were excised at the limbus using a sharp scalpel. Samples were bisected and then immediately fixed in Karnovsky's solution (1.25% glutaraldehyde and 1.0% paraformaldehyde). After 48 hours of fixation, the corneas underwent a serial dehydration using graded alcohol concentrations. With a critical-point drying apparatus, the alcohol was exchanged for anhydrous carbon dioxide. The dried samples were then mounted and coated with 15 μm of gold. Documentary photographs were obtained (magnification, 1000×; working distance, 25 mm) and examined by the same observer masked to the treatment group from which they had been obtained. For light microscopy, after usual preparation, sections were stained in standard fashion by hematoxylin-eosin and periodic acid-Schiff.

To quantitate the histologic changes observed 24 hours postoperatively, sections were placed under a light microscope (Zeiss, Oberkochen, Germany). The deepithelialized zone was studied in sections, divided into anterior and posterior stroma. Cells were quantitated in each of these corneal fields under a magnification of 100×. Counts of keratocytes and studies of morphologic changes observed in these cells were performed in both the individual areas and the results compared. Photomicrographs were taken using a Zeiss Photomicroscope III.

For quantification of normal stromal cells in the cornea in the stained sections, an experienced ophthalmic pathologist, masked as to animal species and treatment protocol, reviewed histologic sections of each cornea and counted the keratocyte nuclei under a magnification of 100× in the anterior and posterior half of the stroma under the deepithelialized area. A reticule in one of the oculars, which contains a 10 mm ruler, was used to mark the beginning and the ending of the cell counting. The projection of the ruler onto the slide comprised 171 μm of stroma. The results of quantification of keratocyte loss observed at 24 hours postoperatively are shown in Table 2. At this point, absence of keratocytes was noticed only in the anterior half of stroma of all corneas, although to different degrees. There was no change in keratocytes of the posterior stroma, either in number or in morphological appearance. In Table 2, the sample size is 2 rabbits per group (for a total of 4 eyes). The number of keratocytes is reported as the means plus or minus the standard deviation.

TABLE 2

Counts of Keratocytes Performed 24 Hours After Deepithelialization in the Anterior Stroma

| Treatment Group | Number of Keratocytes |
| --- | --- |
| 1: Saline drops | 76.0 ± 23.0 |
| 2: Optisol™ drops | 81.5 ± 45.9 |
| 3: MediLens™ soaked in sterile saline plus saline drops | 122.5 ± 53.1 |
| 4: MediLens™ soaked in Optisol™ plus Optisol™ drops | 158.0 ± 65.5 |
| 5: SurgiLens™ soaked in sterile saline plus saline drops | 120.3 ± 69.1 |
| 6: SurgiLens™ soaked in Optisol™ plus Optisol™ drops | 157.3 ± 72.3 |

In Group 1, which served as a control, there was a relatively smooth corneal surface and a marked reduction in numbers of keratocytes. The remaining keratocyte nuclei within the superficial central stroma, beneath the zone of deepithelialization, appeared pyknotic compared to those under the intact epithelium. Light microscopic examination of corneas treated every four hours with keratocyte maintenance solution revealed comparable numbers of keratocytes in the anterior stroma. While there was a relative preservation of keratocytes in the anterior stroma in animals treated with either MediLens™ (Group 3) or SurgiLens™ (Group 5) soaked in saline solution, significantly higher numbers of keratocytes were observed in groups treated with MediLens™ (Group 4) and SurgiLens™ (Group 6) soaked in Optisol™ solution.

The collagen shields were observed to dislocate in six of the 16 eyes between the eighth and twelfth hours and were immediately replaced. Tarsorrhaphy was performed in all rabbits at twelfth hour postoperatively to avoid losing the shields. There was mild to moderate conjunctival injection and edema in all of the eyes during the twenty-four hours of the experiment, with no differences between the groups. These inflammatory changes were attributed to the wounding itself and not to the collagen shields, as there was no apparent difference between the control and treated groups in this respect. There was no evidence of infection in any of the eyes. There was minimal disruption of the anterior stroma after acute injury. The normal lamellar architecture persisted, and the keratocytes degenerated and disappeared only in the anterior stroma. The histopathologic structure of the areas outside the ablated zones were normal in all corneas examined. No abnormalities were seen in posterior stromal keratocytes and the endothelium was normal in all eyes.

EXAMPLE 3

Evaluation of Artificial Tear Compositions as Keratocyte Maintenance Solutions

Various artificial tear solutions are evaluated for use as keratocyte maintenance solutions. Samples from keratocyte cell cultures were brought into contact with compositions A–H (artificial tear compositions). Compositions A–H are characterized by the polymer and salt components and the osmolarity. Compositions A–D were found not to induce any significant damage to keratocytes; on the other hand, compositions E–H were found to be lethal to the cultured keratocytes. The compositions are described in Table 3.

TABLE 3

Artificial Tear Compositions

| Composition | Polymer | Salts | Osmolarity (mOsm) |
|---|---|---|---|
| A | 1.0% carboxymethylcellulose | $CaCl_2$, KCl, NaCl, Na lactate | 295 |
| B | 0.5% carboxymethylcellulose | $CaCl_2$, $MgCl_2$, KCl, NaCl, Na lactate | 284 |
| C | 0.1% dextran 70; 0.3% hydroxypropylcellulose | $CaCl_2$, $MgCl_2$, $ZnCl_2$, $NaHCO_3$, KCl, NaCl, HCl, NaOH, $CO_2$ | 275 |
| D | 0.3% glycerin | $CaCl_2$, $MgCl_2$, $ZnCl_2$, KCl, NaCl, Na citrate, Na phosphate | 261 |
| E | 0.1% dextran 70; 0.3% hydroxypropylmethylcellulose | KCl, NaCl, HCl, Na borate, NaOH | 273 |
| F | 1% polyvinyl alcohol; polyethylene glycol 400 | edetate disodium; dextrose | 257 |
| G | 0.5% polyvinyl alcohol; 0.6% povidone | KCl, NaCl, $NaHCO_3$, dextrose, Na borate, Na phosphate | 248 |
| H | 0.2% polyethylene glycol 400; 0.1% dextran | NaCl; edetate disodium; NaOH; polycarbophil | 227 |

As a review of Table 3 makes apparent, compositions A–D are distinguished on the basis of an osmolarity over 250 mOsm and at least one calcium and/or magnesium salt.

While there have been shown and described the fundamental novel features of the invention, it will be understood that various omissions, substitutions and changes in the form and details illustrated may be made by those skilled in the art without departing from the spirit of the invention. It is the intention, therefore, to be limited only as indicated by the scope of the following claims.

What is claimed is:

1. A method for preventing keratocyte loss after injury or trauma to corneal epithelium, which method comprises applying to the cornea a keratocyte maintenance solution under conditions effective to enhance keratocyte viability by maintaining normal keratocyte metabolism over a period of time sufficient to permit corneal wound healing, said keratocyte maintenance solution having an osmolarity of at least about 250 mOsm and comprising at least one ion selected from magnesium or calcium, wherein said keratocyte maintenance solution is free of serum and glutathione.

2. A method according to claim 1, wherein the osmolarity is at least about 280 mOsm.

3. A method according to claim 2, wherein the osmolarity is at least about 320 mOsm.

4. A method according to claim 1, wherein the keratocyte maintenance solution comprises at least one non-immunogenic neutral or negatively-charged macromolecule.

5. A method according to claim 4, wherein the at least one macromolecule is selected from the group consisting of chondroitin sulfate, dermatan sulfate, dermatin sulfate, heparin sulfate, heparan sulfate, keratin sulfate, keratan sulfate, hyaluronic acid, dextran, dextran sulfate, polyvinyl pyrrolidone, polyethylene glycol, polyvinyl acetate, hydroxypropyl cellulose, hydroxypropylmethyl cellulose, carboxymethyl cellulose and carboxypropylmethyl cellulose.

6. A method according to claim 4, wherein the at least one macromolecule is present in a concentration of about 0.1% to about 10% by weight of the keratocyte maintenance solution.

7. A method according to claim 1, wherein the keratocyte maintenance solution is a corneal storage medium.

8. A method for preventing keratocyte loss after injury or trauma to cornea epithelium, which method comprises applying to the cornea a keratocyte maintenance solution under conditions effective to enhance keratocyte viability by maintaining normal keratocyte metabolism over a period of time sufficient to permit corneal wound healing, said keratocyte maintenance solution having an osmolarity of at least about 250 mOsm and comprising at least one ion selected from magnesium or calcium, wherein said keratocyte maintenance solution is free of serum and glutathione, wherein the keratocyte maintenance solution comprises: an aqueous electrolyte solution; a glycosaminoglycan in a range of 0.01 mg/ml to 100 mg/ml; a deturgescent agent in a range of 0.01 mg/ml to 100 mg/ml; an energy and carbon source in a range of 0.05 mM to 10 mM; and a buffer system in a range of 0.1 mM to 100 mM.

9. A method according to claim 8, wherein the keratocyte maintenance solution further comprises one or more of: an antioxidant in a range of 0.001 mM to 10 mM; membrane stabilizing agents in a range of 0.01 mg/ml to 500 mg/ml; antibiotics and/or antimycotic agents in a range of 0.1 µg/ml to 1 mg/ml; ATP precursors in a range of 0.001 mM to 10 mM; and nutrient cell supplements in a range of 0.001 mM to 10 mM.

10. A method according to claim 1, wherein the keratocyte maintenance solution is maintained over the cornea as a fluid bath.

11. A method according to claim 1, wherein the keratocyte maintenance solution is maintained in contact with the cornea by means of an absorbent material effective for controlled release of the keratocyte maintenance solution.

12. A method according to claim 11, wherein the absorbent material is a collagen shield.

13. Apparatus for preventing keratocyte loss after injury or trauma to corneal epithelium, comprising a piece of absorbent material adapted to fit over at least a portion of the cornea impregnated with a keratocyte maintenance solution, said material being effective for controlled release to the cornea of the keratocyte maintenance solution impregnated therein, said keratocyte maintenance solution being effective to enhance keratocyte viability by maintaining normal keratocyte metabolism over a period of time sufficient to permit corneal wound healing, said keratocyte maintenance solution having an osmolarity of at least about 250 mOsm and comprising at least one ion selected from magnesium or calcium, wherein said keratocyte maintenance solution is free of serum and glutathione, wherein the keratocyte maintenance solution comprises: an aqueous electrolyte solution; a glycosaminoglycan in a range of 0.01 mg/ml to 100 mg/ml; a deturgescent agent in a range of 0.01 mg/ml to 100 mg/ml; an energy and carbon source in a range of 0.05 mM to 10 mM; and a buffer system in a range of 0.1 mM to 100 mM.

14. Apparatus according to claim 13, wherein the keratocyte maintenance solution further comprises one or more of: an antioxidant in a range of 0.001 mM to 10 mM; membrane stabilizing agents in a range of 0.01 mg/ml to 500 mg/ml; antibiotics and/or antimycotic agents in a range of 0.1 µg/ml to 1 mg/ml; ATP precursors in a range of 0.001 mM to 10 mM; and nutrient cell supplements in a range of 0.001 mM to 10 mM.

* * * * *